United States Patent
Sandholdt

(10) Patent No.: US 8,013,750 B2
(45) Date of Patent: Sep. 6, 2011

(54) DEVICE FOR DETECTING HAEMATOMA OR SUBCUTANEOUS HAEMORRHAGE AFTER PERCUTANEOUS CORONARY INTERVENTION

(76) Inventor: Carsten Sandholdt, Arendai (NO)

( * ) Notice: Subject to any disclaimer, the term of this patent is extended or adjusted under 35 U.S.C. 154(b) by 434 days.

(21) Appl. No.: 12/280,351

(22) PCT Filed: Feb. 23, 2007

(86) PCT No.: PCT/NO2007/000069
§ 371 (c)(1),
(2), (4) Date: Aug. 22, 2008

(87) PCT Pub. No.: WO2007/097635
PCT Pub. Date: Aug. 30, 2007

(65) Prior Publication Data
US 2010/0231377 A1 Sep. 16, 2010

(30) Foreign Application Priority Data
Feb. 24, 2006 (NO) .................................. 20060916

(51) Int. Cl.
*G08B 21/00* (2006.01)
(52) U.S. Cl. ............... 340/626; 340/539.12; 600/371; 602/41
(58) Field of Classification Search ............ 340/604, 340/605, 626, 539.1; 600/371, 307
See application file for complete search history.

(56) References Cited

U.S. PATENT DOCUMENTS

| | | | |
|---|---|---|---|
| 3,853,118 A | 12/1974 | Schendel | |
| 5,497,787 A | 3/1996 | Nemesdy et al. | |
| 5,579,765 A * | 12/1996 | Cox et al. | 600/307 |
| 5,790,036 A | 8/1998 | Fisher et al. | |
| 6,360,615 B1 * | 3/2002 | Smela | 73/862.474 |
| 6,445,304 B1 | 9/2002 | Bandeian, Jr. et al. | |
| 2002/0094701 A1 | 7/2002 | Biegelsen et al. | |
| 2008/0004904 A1 * | 1/2008 | Tran | 705/2 |

FOREIGN PATENT DOCUMENTS

| | | |
|---|---|---|
| DE | 40 14 572 A1 | 11/1991 |
| WO | 2005/067796 A1 | 7/2005 |

* cited by examiner

*Primary Examiner* — Jennifer Mehmood
*Assistant Examiner* — Hongmin Fan
(74) *Attorney, Agent, or Firm* — Young & Thompson

(57) ABSTRACT

A device for detecting a hematoma or subcutaneous hemorrhage after a PCI, which includes a bandage provided with fastening elements for its placement at the PCI access site, and the use of a safety bandage for producing the same. In the device, the bandage includes a flexible and, in its longitudinal direction, non-elastic element connected to a strain sensor so arranged that the strain sensor, when the element after the placement of the bandage at the access site is subjected to a change in tension as a result of a hematoma or subcutaneous hemorrhage after the PCI, emits a signal that is indicative of the hematoma or hemorrhage.

22 Claims, 12 Drawing Sheets

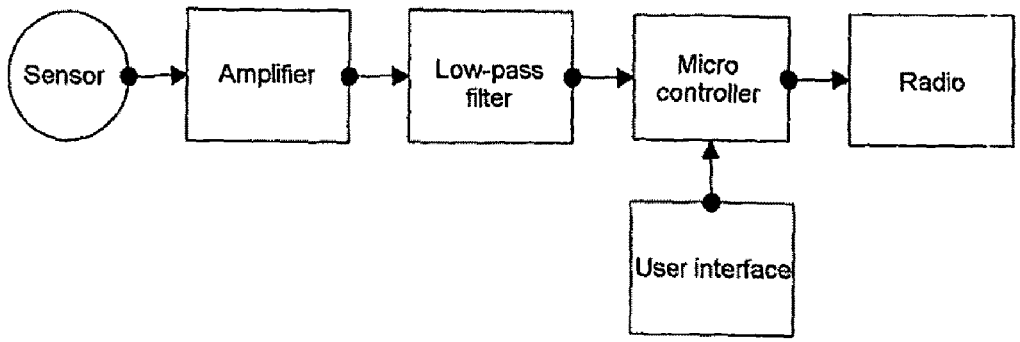
Fig. 6
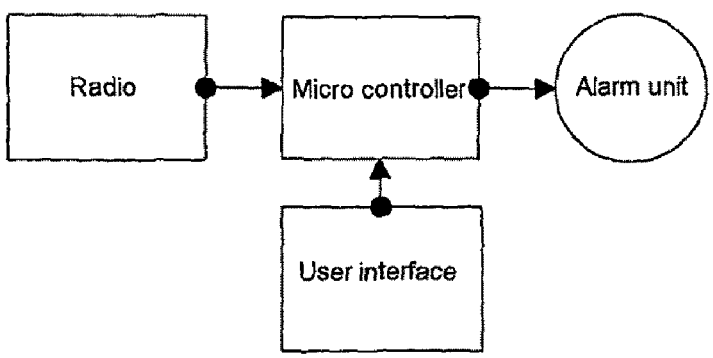
Fig. 7
| Function | Cable colour | RJ11 connector |
|---|---|---|
| Exc- | Blue | 4 |
| Exc+ | Green | 1 |
| Meas- | Red | 2 |
| Meas+ | Yellow | 3 |
Fig. 8

| Pin no. | Port | Function |
|---|---|---|
| 20 | 2.0 | Connection of pushbutton switch |
| 5 | 6.6 | Test point, can emit an analogue signal |
| 6 | 6.7 | Test point, can emit an analogue signal |
| 10 | | 2V reference voltage |
| 59 | 6.0 | Input terminal for analogue measuring signal |
| 60 | 6.1 | Sampling of voltage in the circuit |
| 54 | - | Connection for JTag |
| 55 | - | Connection for JTag |
| 56 | - | Connection for JTag |
| 57 | - | Connection for JTag |

| Port 1,3,5 | Reserved for communication with radio unit. | |
| Port 2 | Reserved for external signals, possibility for interruption | |
| Port 6 | Reserved for ADC and DAC | |

| | Value | Unit |
|---|---|---|
| Power consumption | Typically 5.5 | mA |
| Transmission frequency | 2400.00 – 2483.50 | Hz |
| Charging current | Max 1.0 | A |
| Input terminals | | |
| ? | | |
| Charging voltage | 3.0 – 4.2 | V |
| Analogue amplification | 205X | |

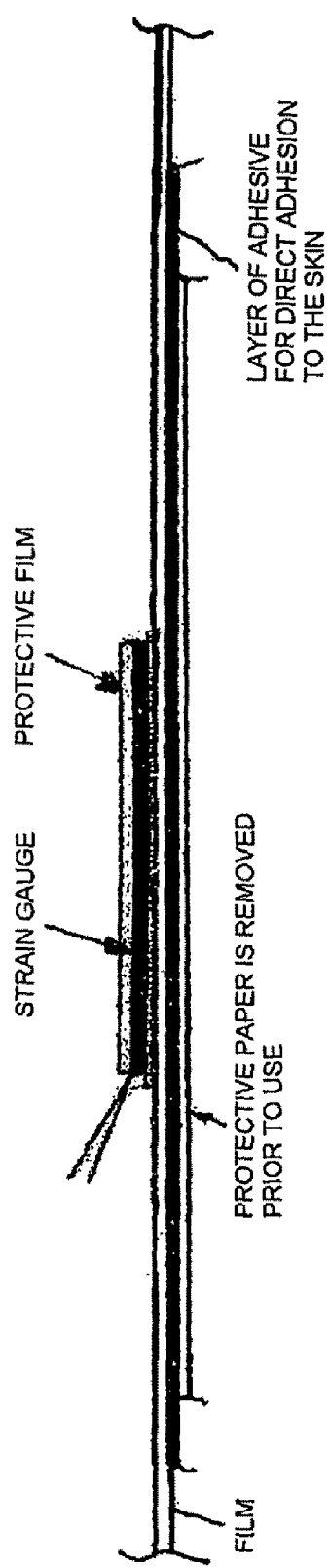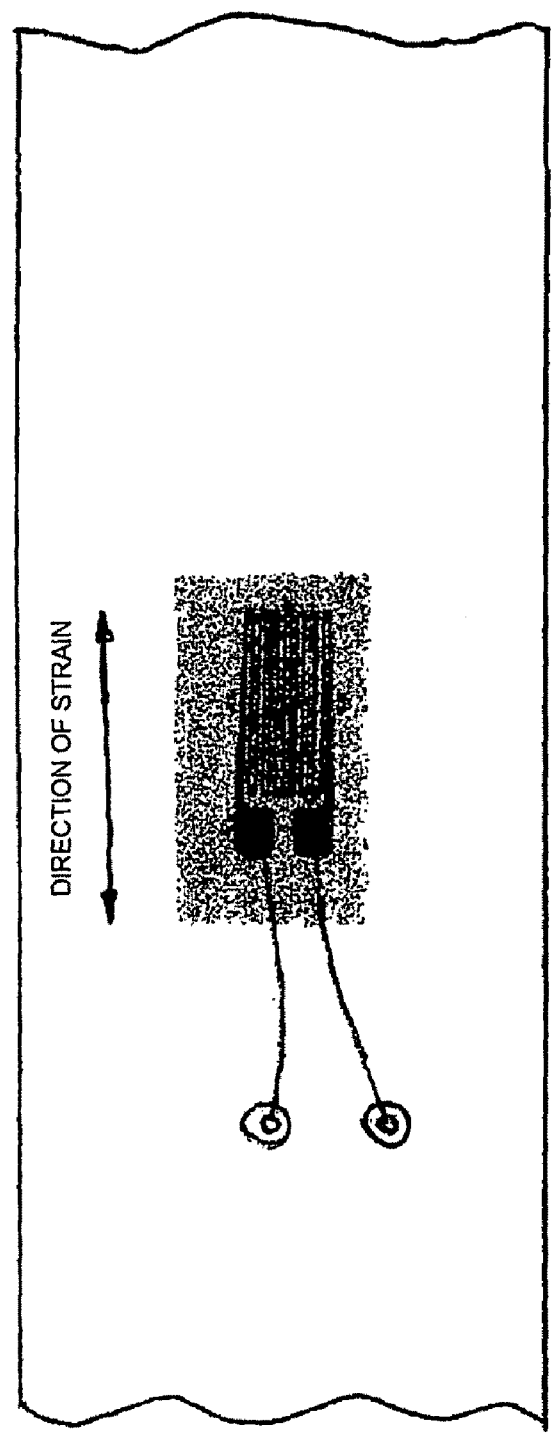
Fig.18a                               Fig.18b

DEVICE FOR DETECTING HAEMATOMA OR SUBCUTANEOUS HAEMORRHAGE AFTER PERCUTANEOUS CORONARY INTERVENTION

In practising his profession as a nurse in an intensive care/coronary care unit, the inventor has been responsible for the care of patients who have undergone a percutaneous coronary intervention (PCI), also referred to as balloon dilation. The intervention may be a diagnostic percutaneous coronary procedure. The inventor saw a need for a way of protecting the patients from after-effects of a PCI, which would make everyday life safer and less stressful for both the patient and the nurse. On the basis of complications that have been seen earlier in patients who have undergone this intervention, the time has come for a product according to the invention, which product may be described as "an elastic safety bandage for reducing complications after a PCI".

When patients suffering from heart disease, often blood clots (thrombi) or other chest pains, undergo a diagnostic percutaneous coronary procedure, this is done by the doctor making a small incision into the artery in the wrist (radial artery or arteria radialis). The doctor passes a fine wire in through the artery, which is then passed all the way to the heart. The doctor sees the progress of wire with X-rays. When the doctor sees that one of the arteries in the heart is perhaps blocked (blood clot) or narrowed (chest pain/angina pain), he can with the aid of other equipment open up the artery. After the intervention has been completed, a compressive bandage is placed on the puncture site. In some cases, the patients have been given blood-thinning medication so as to prevent other blood clots post procedure. In these cases there is a great risk of internal bleeding at the puncture site. The compressive bandage may sometimes be a little askew or become slightly loose. As a result, substantial internal bleeding can occur in the forearm or hand, in that the artery ruptures and blood flows out wherever it finds space. It is not certain that the hole in the skin will rupture, and therefore a large bruise (haematoma) occurs, which in some cases needs to be evacuated, i.e., a surgical intervention of a slightly greater magnitude. In other cases the skin ruptures too, but the compressive bandage prevents the blood from spurting. If the patient is sleeping or in some other way is not quite "with it" after the intervention, which may be the case as some patients are given a mild sedative before the intervention, there is also a risk that they may therefore not notice the rupture of the artery in the wrist. In just a few minutes, the patient can lose a great deal of blood, enough perhaps to require a transfusion.

The present invention provides a device for use to detect an abnormal state, in particular a haematoma or a haemorrhage in a part of a patient who has undergone a percutaneous coronary intervention, also referred to as balloon dilation, which device is characterised by the features that are set forth in appended independent claim 1.

Additional advantageous features of the present inventive device for use in detecting an abnormal state, in particular a haematoma or a haemorrhage, in a part of a patient who has undergone a PCI, also referred to as balloon dilation, are set forth in appended dependent claims 3-19.

The invention provides methods for the manufacture of a PCI access site pressure bandage device or a PCI access site safety bandage device characterised by the features set forth in claims 20 and 21.

The invention will be explained in more detail below with reference to the attached figures, wherein:

FIG. 6 shows in the form of a block diagram a transmitter unit for one embodiment of the invention;

FIG. 7 shows in the form of a block diagram a receiver unit for one embodiment of the invention;

FIG. 8 shows in table form a connection scheme for a sensor for an exemplary embodiment of the invention;

Figure 20:
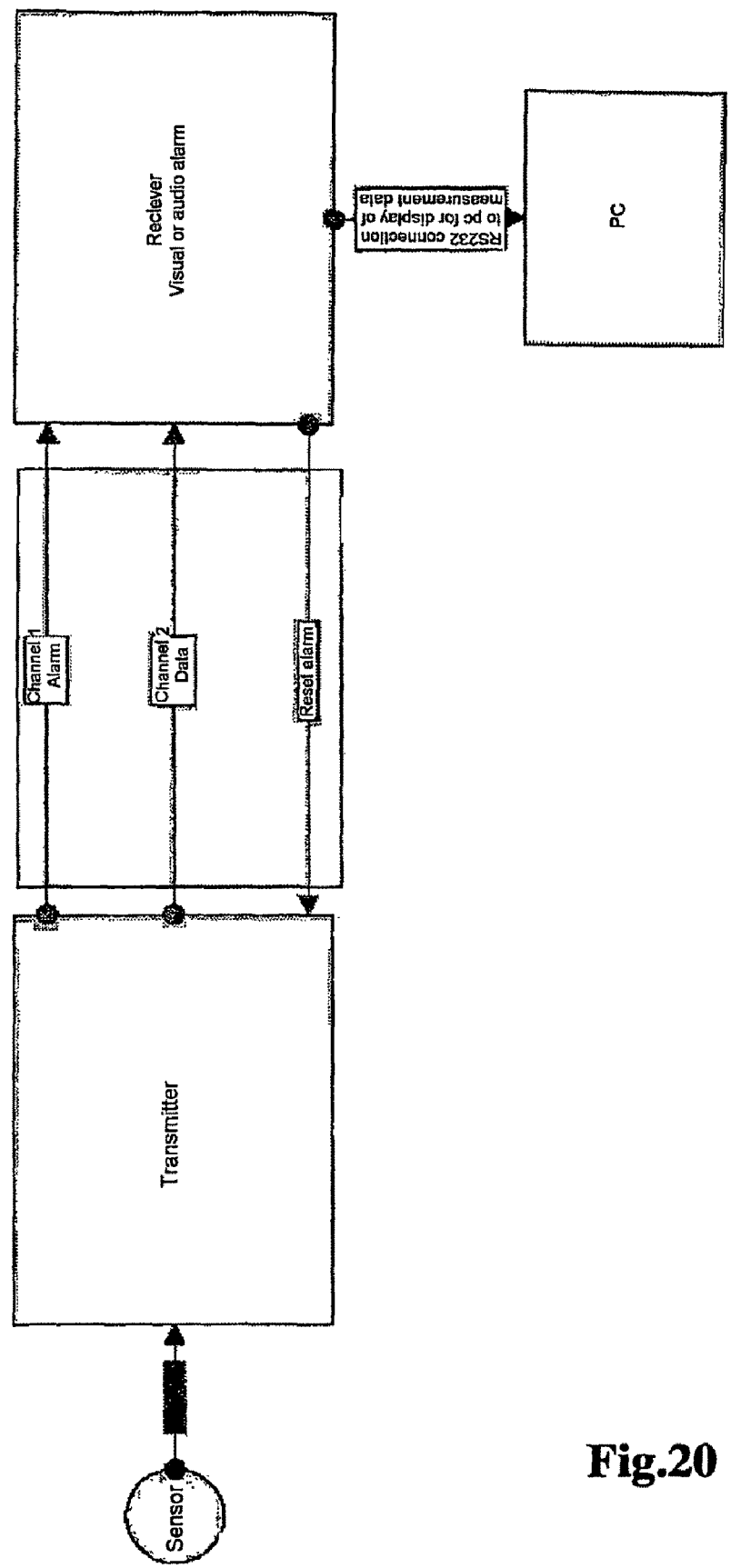
Figure 21:
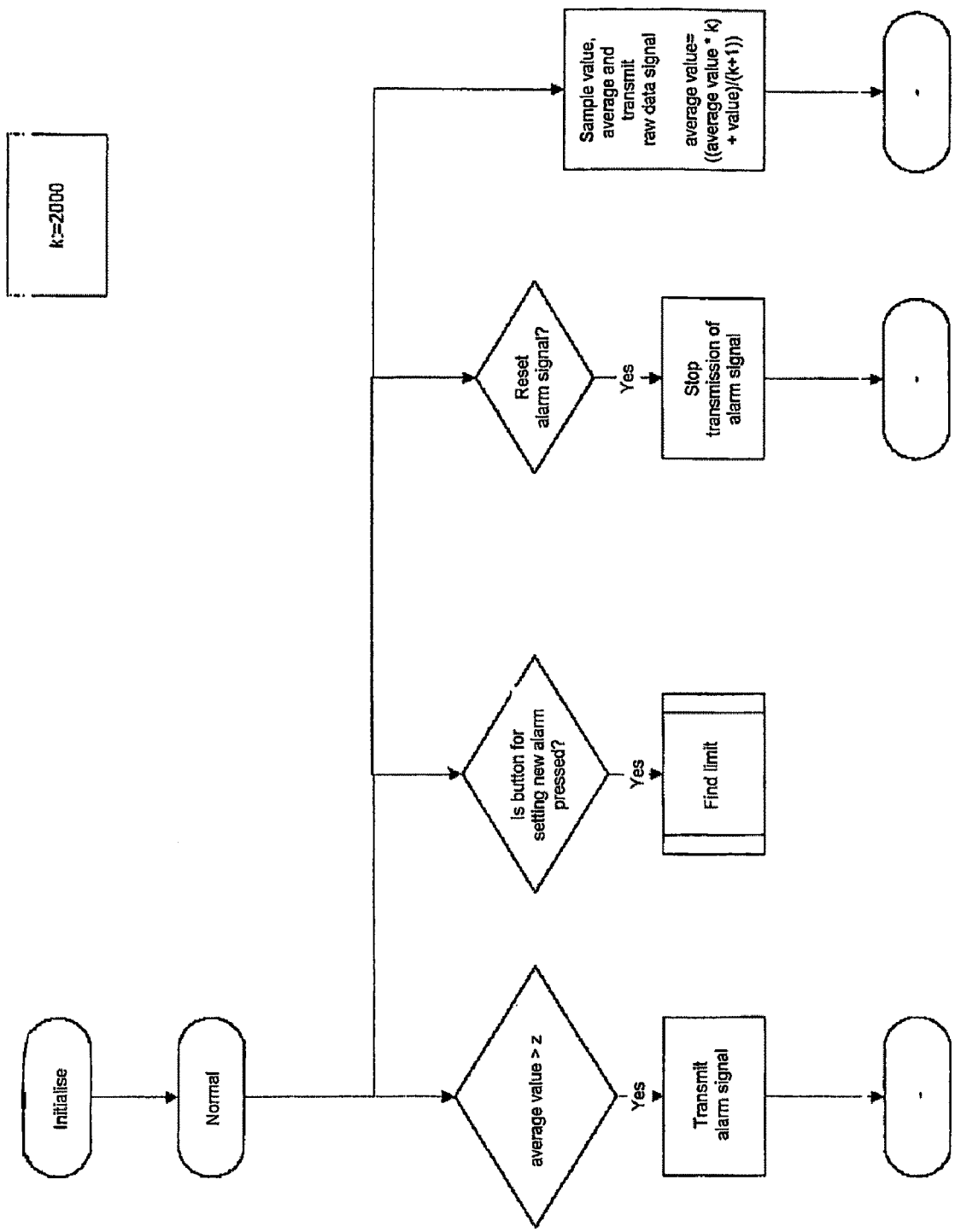

FIGS. 18 a and b are a sectional view and a plan view, respectively, of a bandage equipped with a strain gauge sensor according to the invention, FIGS. 19 a, b, c and d illustrate in a circuit diagram form amplifier and filter circuits for the strain sensor signal, passive-connected amplifiers, and connection for reference voltage generation in an exemplary embodiment of the invention;

FIG. 20 illustrates in the form of a block diagram an overall system for detection and warning in accordance with the invention; and FIG. 21 illustrates in a flow chart an example of a collection of processes and procedures that are executed in the microcontroller.

A product according to the invention gives an alarm when it is placed around the forearm which becomes distended or develops a swelling, as a consequence of a haematoma, or becomes wet as a consequence of bleeding. The patient still needs quite frequent monitoring, but certainly not as frequent as before. Now the nurse, after having a "peep" at the patient, can calmly return to other tasks, with the assurance that in the event of any complications, the alarm will go and extra compression will be required.

Figure 1:
FIG. 1 is a picture, in an extended, flat state, of the outside of an elastic bandage which has woven or braided therein metal wires connected to a strain sensor for one embodiment of the invention.
Figure 2:
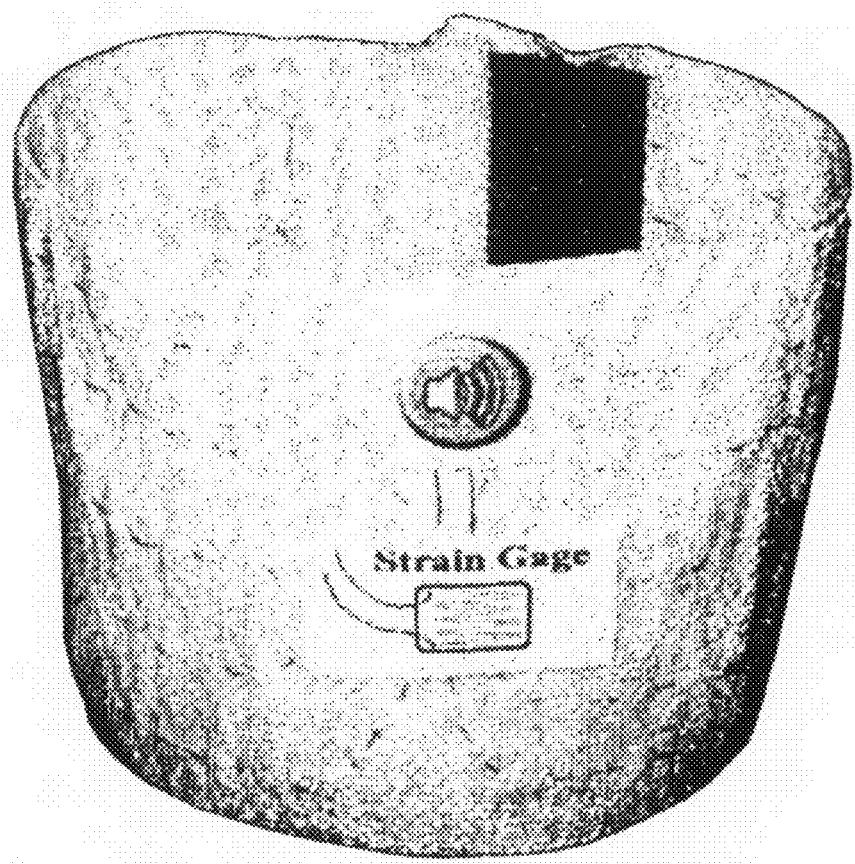
FIG. 2 is a picture of the elastic bandage shown in FIG. 1, in a circular state, with its ends almost joined.
Figure 3:
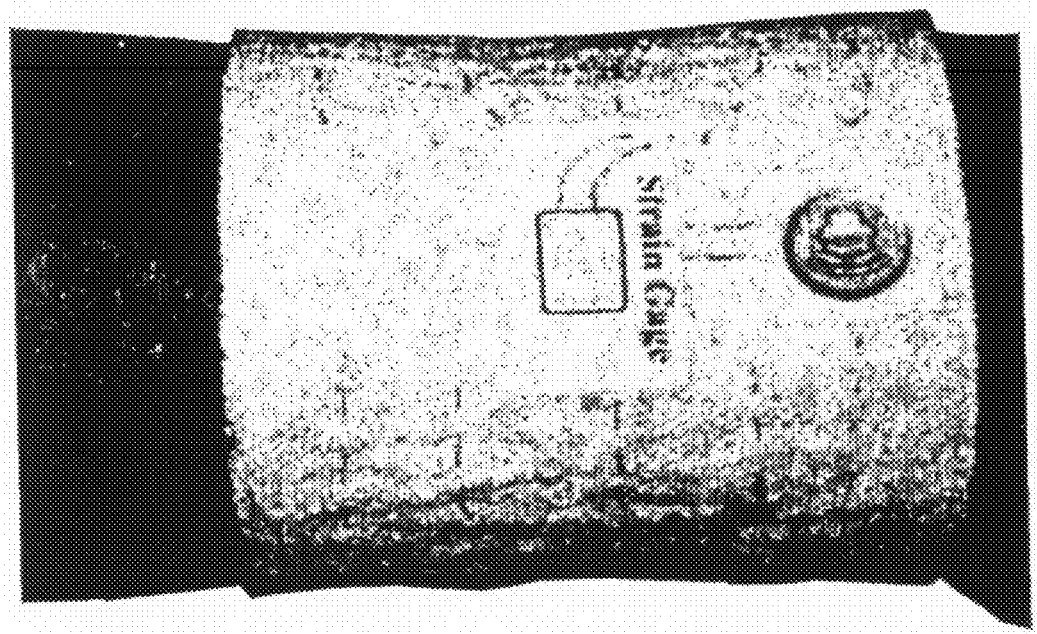
FIG. 3 is a picture of the elastic bandage shown in FIGS. 1 and 2, in a circular state and placed around a forearm, with its ends joined to maintain the circular shape.
Figure 4:
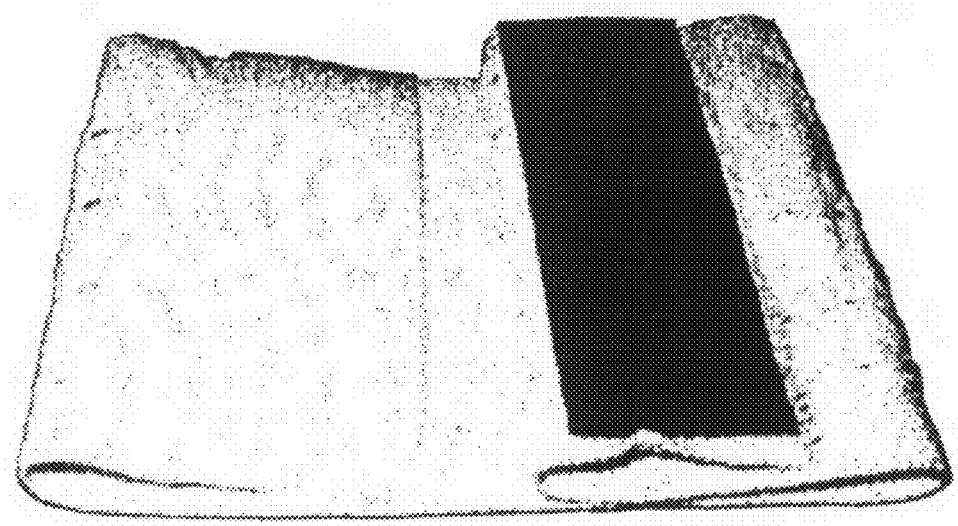
FIG. 4 is a picture of a hook and loop fastening tape arranged on the ends of the elastic bandage shown in FIGS. 1, 2 and 3, as a means for joining the end areas of the elongate elastic bandage to form a continuous circular shape as shown in FIGS. 2 and 3.
Figure 5:
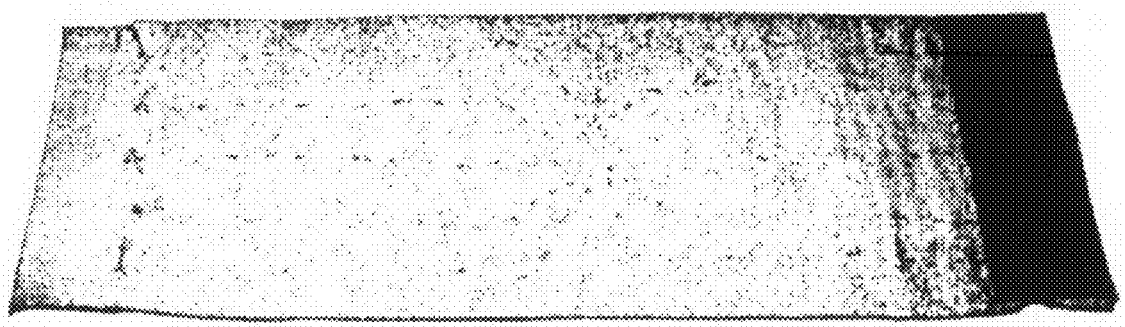
FIG. 5 is a picture, in an extended, flat state, of the inside of the elastic bandage in which there are woven or braided metal wires connected to a strain sensor for one embodiment of the invention.

Various aspects of the invention can be explained by means of the following examples An elastic bandage has woven or braided therein metal wires that are connected to an electronic device, a strain gauge, which in turn is connected to high-frequency, audio signal (FIG. 2). When the elastic bandage is subjected to tension or moisture, this will induce strain on the strain gauge, which then converts this strain into a high-pitched tone (FIG. 3). A hook and loop fastener is sewn on at each end of the elastic bandage as closing mechanism (FIGS. 1, 4-5). There is tighter elastic in the edge of the elastic bandage oriented towards the elbow. This provides a delimitation of the complication area, which makes it easier to measure distension since the blood has a smaller expansion area.

The invention is able to make use of elements that are already known:

1. Strain gauge—Is found in other contexts.
2. Elastic bandage—Is used for other purposes.
3. Audio signal—Is found in smoke detectors, among other things.
4. Hook and loop fastener—Is commonly known.

However, these articles put together as shown in the attached picture reproduced in FIGS. 1-5 provide a useful new product for which patent is hereby sought.

Explained briefly, the technology of the invention can be implemented as:

An elastic bandage has woven-in metal wires that are connected to a strain sensor, also called a strain gauge. This is turn is connected to an audio signal device which will emit a high-frequency signal if the elastic bandage is expanded or becomes wet.

Thus, the elastic bandage, which according to the invention comprises woven-in metal wires connected to a strain sensor, seems in terms of appearance and use to be extremely similar to the standard elastic bandages which have previously been used as safety bandage after a PCI.

Following a PCI, it has been found in as many as one in five cases that expansion or moisture may occur in that the artery in the wrist ruptures and the blood thus flows out into the subcutis or out through the puncture site in the skin. This poses a danger to the health of the patient. The abnormal state may occur some time after the intervention has taken place, but can develop into a dangerous condition in the course of a few minutes.

Once the intervention has been completed a pressure bandage is placed over the puncture site, which will often be the radial artery (artery in the wrist). Then a safety bandage is placed behind or over this pressure bandage at the radial artery, i.e., about 5-7 cm from the wrist. If a rupture of the artery occurs, blood will flow out into the surrounding tissue and, as stated above, will in the course of a few minutes cause a swelling.

In somewhat fewer cases, the femoral artery (arteria femoralis), the artery in the groin, is used as entry site for carrying out a PCI. At the femoral artery, a safety bandage is normally applied as close to the puncture site as possible. It is in this area that a swelling as a consequence of an artery rupture or bleeding, especially represented by a haematoma, will be detected by a safety bandage according to the invention.

With regard to detection, mention can be made of the following aspects of the invention.

According to a first aspect, the safety bandage of the invention may comprise an elastic bandage which has woven or braided therein metal wires that are connected to an electronic device such as a strain sensor, a strain gauge. When the elastic bandage is subjected to tension or moisture, this will induce strain on the strain gauge. For placement of the elastic bandage, a hook and loop fastener is sewn on at each end thereof as closing mechanism. In one embodiment which is to be used in connection with transradial PCIs, there is preferably tighter elastic at the edge of the elastic bandage that is to be oriented towards the elbow. In this way, a delimitation of the complication area is obtained, which makes it easier to measure tension as a result of swelling caused by haematoma, since the blood has a smaller expansion area.

According to another aspect, the inventive safety bandage equipped with strain gauge technology, may consist of a "plastic film" with tape or other adhesive means adhered thereto to enable it to adhere to the skin. A strain sensor, such as a strain gauge is glued to this film. A strain gauge that will measure to a thousandth of a millimeter is preferably used.

To obtain a measurement of optimal accuracy, there are certain factors that must be eliminated. On exposure to heat, which will occur when the bandage is applied to a patient, the equipment will give an alarm in response to thermal expansion or contraction. Therefore, after the bandage has been applied, the patient will be asked to clench and open his hand. The safety bandage will thus be subjected to a tension that can be ascribed to a change in temperature on application, and muscular movement, and the apparatus can be set to zero to compensate for such effects. After zero setting with a clenched and/or open hand, which leads to a "normal" tension in the bandage and establishment of a "normal" limit value, the sensing will be in negative value, but will not give an alarm on heat expansion as expansion resulting from heat from the patient is not sufficient to affect the limit value just set.

In the event of a haemorrhage, however, the set limit value is exceeded as the haemorrhage or swelling will result in greater pressure against the bandage than the pressure that the patient has produced by opening and clenching his hand.

According to another aspect, the inventive safety bandage may include the use of an optical sensor. The inventor has experienced that in the event of bleeding in the groin, the swelling will take place more slowly because of the relatively large surrounding tissue. By also using optical transillumination and/or illumination of the skin, it will be possible to detect the bleeding in the surrounding tissue with optical means, and be better able to discover the haemorrhage, possibly even before the swelling occurs to such an extent that it can be detected by the strain sensor.

According to a further aspect, the inventive safety bandage may also include the use of a temperature sensor, which will register a change in temperature in connection with an extravasation of blood into the skin. This could be integrated into both of the two cases mentioned above.

The technology used for signal transmission from the location of the applied sensor to the alarm location may be transmission via radio signal/wirelessly. This may depend upon the physical conditions at each hospital, but with the possibility of relaying a radio signal through "repeat-systems", the most remote corners can be reached.

The values that the sensors measure are transmitted to a digital part, where the data is processed in a microprocessor. A signal from one or more strain gauges, the optical sensor and/or the temperature sensor can be amplified, filtered and optionally digitalised before it is transmitted to a signal processing unit. The signals may then be combined or processed in such manner that, for example, in the case of pressure against the bandage that is detected by the strain gauge, the pressure must be over a certain limit value for a certain time period in order to trigger the signal. In this way, relatively brief and external influences are eliminated, such as for example that that sensor comes under pressure as the patient moves.

Below is an explanation of an example of a system according to the invention for detecting and warning of a haemorrhage, in particular a haematoma, after a PCI.

An example of the system is shown in FIGS. 6 and 7. The system comprises what is referred to herein as a transmitter unit, as shown in FIG. 6, and a receiver unit, as shown in FIG. 7.

An example of the whole system is also shown in FIG. 20, where measurement data is sampled from a strain gauge and the data is transmitted to a receiver which is able to show the data directly on a PC. The transmission protocol used in the example is a proprietary protocol for WPR Medical, called WFEP. WFEP can transmit data on several channels at the same time. In this example, channel 1 is used to transmit data in order to be able to trigger an alarm in the receiver. Channel 2 is used to transmit raw data. The protocol is two-way and reset of the alarm signal can be sent as a response from receivers on channel 1.

The transmitter unit, such as that illustrated in FIG. 6, is placed on the patient for registering and preprocessing sensor signals. The receiver unit, such as that illustrated in FIG. 7, is located in connection with the monitoring staff who are to be warned in the event of an abnormal patient condition, such as when a haematoma is developing.

In a preferred embodiment of the invention, the analogue measuring circuit in the transmitter unit, see FIGS. 6, 19a, 19b, 19c and 19d, will consist of an INA122 operation amplifier where the input terminals are connected to a measuring bridge in a strain gauge. The operation amplifier amplifies the signal and the signal is filtered in order to prevent anti-aliasing before it is sampled in a microcontroller. The digital signal is processed so that an alarm can be given. For more details about the digital signal processor, reference is made to the following description of the signal processing process, which is implemented as a computer program for the microcontroller.

A user interface is connected to the microcontroller in order to provide the possibility of checking the system and setting limit values. If an abnormal situation arises, the system sends, via the radio unit, an alarm sign to a receiver unit.

The transmitter can easily be divided into two parts, an analogue part consisting of a sensor (e.g. a strain gauge with measuring bridge), amplifier and low-pass filter, and a digital part with microcontroller, radio and user interface.

The receiver unit, as shown in FIG. 7, has a corresponding radio system so that it can communicate with the transmitter. It is preferably also provided with a microcontroller, a user interface and an alarm unit. The alarm unit may be light, sound, vibration or the like. There may also be a connection to existing alarm equipment.

However, for a first prototype, it is preferable to use a so-called "standard WPR receiver", with audio signal. This receiver and its associated transmitter work in accordance with a wireless transmission protocol provided by WP Medical. Reference is made to WP Medical for a description of the aspects which relate to wireless transmission.

Below, with reference to FIGS. 19a-d, follows a more detailed explanation of the realisation of the invention using a strain gauge with measuring bridge.

U9 produces a constant reference voltage of 2V. This is broken down to 1V through a voltage divider and a buffer in the OPA4336 circuit. The 1V voltage in the buffer is connected to Exc+, whilst Exc− is connected to earth. Meas− and Meas+ are connected to corresponding input terminals on INA122. The input impedance on INA122 is about $10^{10}$ ohm.

Connection to the transmitter unit is done in accordance with the table shown in FIG. 8.

The amplifier function will now be explained. The analogue measuring circuit consists of an INA122 operation amplifier where the input terminals are connected to the measuring bridge in the strain gauge. The reference signal to INA122 is connected to earth, but it can be reconnected to the 1V reference signal by moving R65 to R66. Amplification is regulated by R3. In this case, amplification of 205× has been chosen.

$$\text{Amplification} = 5 + \frac{200\ k}{Rg} = 5 + \frac{200E3}{1E3} = 205$$

Figures 9, 10:
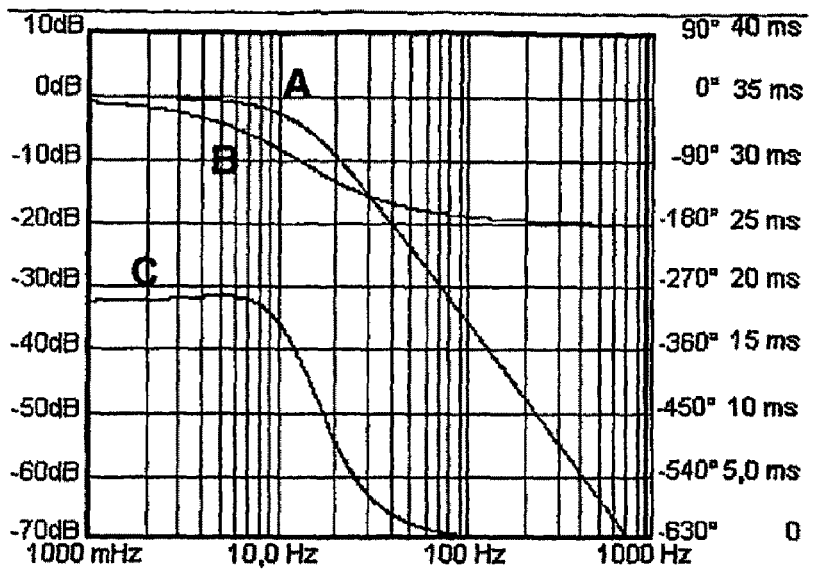
FIG. 9 shows by means of plotted graphs the characteristics of a low-pass filter for an exemplary embodiment of the invention.
FIG. 10 shows in table form a connection scheme for ports and connections for a controller in an exemplary embodiment of the invention.

The low-pass filter function will now be explained with reference to FIG. 9. In FIG. 9 the following curves are shown: curve A indicating strain (dB), curve B indicating phase response (degrees), and curve C indicating time delay (ms). A low-pass filter is constructed around OPA4336. The most important function is to prevent anti-aliasing when the signal is to be sampled and digitalised. After a preliminary evaluation of the signal, a Sallen-Key filter with a limiting frequency of 10 Hz is chosen, since it is the DC level that changes when the strain gauge is subjected to tension. The sampling frequency used, however, is 500 HZ, i.e., that the filter can be increased to 250 Hz and that all filtering is done digitally.

The action of the microcontroller will now be explained with reference to FIG. 10. The system is connected to a MSP430F168 microprocessor from Texas. In principle, any microprocessor can be used. A pushbutton switch is connected to enable a limit value to be stored. The microcontroller can be programmed through the JTag interface in connection J1.

Specific connections to the microcontroller are as shown in FIG. 10.

Figures 11, 12, 13:
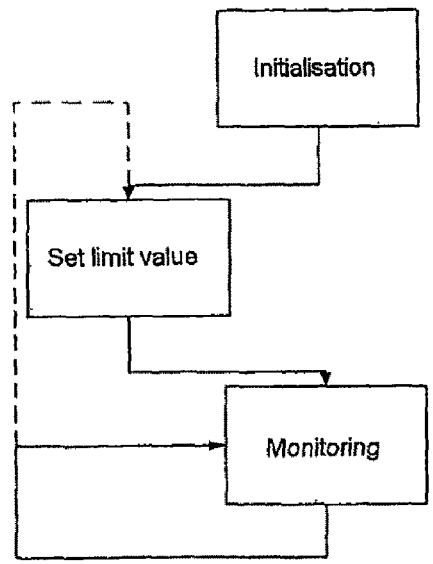
FIG. 11 shows in table form a connection scheme for additional ports and connections for a controller in an exemplary embodiment of the invention.
FIG. 12 shows in a table form operating specifications for an exemplary embodiment of the invention.
FIG. 13 shows a flow diagram to illustrate the general procedure that is executed in a microcontroller in an exemplary embodiment of the invention.

The distribution of the microcontroller ports is as shown in FIG. 11.

Below follows an explanation of the resolution of the digital signal. The microcontroller has an inbuilt 12 bits ADC to render the signal from the strain gauge digital. The reference voltage used is 2V. This corresponds to a resolution of 0.48 mV/bit. Since the signal is analogously amplified by a factor of 205, this will mean that the smallest change that can be detected is 0.0024 mV. The strain gauge has a K factor of 2. This corresponds to 2 mV/V=4000 um/m. If the strain gauge is stretched one millimeter, this will give a result of 2 mV. Thus, 2 mV will correspond to a digital value of 833. If the strain gauge is subjected to tension that exceeds 4.92 millimeters, it will go into saturation. If a change of 5 millimeters is found to be too small, either the analogue amplification can be lowered or the digital reference signal can be put at 3V.

To be able to maintain a stable voltage and charge the battery, a regulator is used. This is selected to deliver 3V. The voltage can be adjusted by the resistors R63 and R64. A lithium polymer rechargeable battery is also connected to the circuit.

The voltage on the electronics can be measured using port 6.1 on the microcontroller. The sampled value will be half of the voltage in the circuit.

Charging the system must only be done using Mascot LI 2241 article no. 2241000047.

Below follows an explanation of some of the transmitter unit's interfaces.

An RJ11 plug is used to connect the strain gauge to the transmitter unit. The connection diagram for this is shown in Chapter 2.

Charging takes place through J5, a connector for a 2.5 mm jack.

The unit can be switched off and on using switch SW2.

SW1 is used to store a new limit value.

The electrical characteristics of the transmitter unit are as indicated in the table shown in FIG. 12.

As mentioned above, signal processing is carried out by a microcontroller for detection of haematoma. For the processing, at least one limit value is set that is used as reference in the detection process.

FIG. 13 illustrates in general the sequence in which the sub-processes that constitute setting and monitoring are executed. The sensor is initialised in that standard values are set up and that peripheral units (receivers) are connected. To start the monitoring, a limit value must be set. When the limit value is set, the monitoring algorithm can be started. The limit value can be changed during the monitoring if there is a need to do so.

Figure 14:
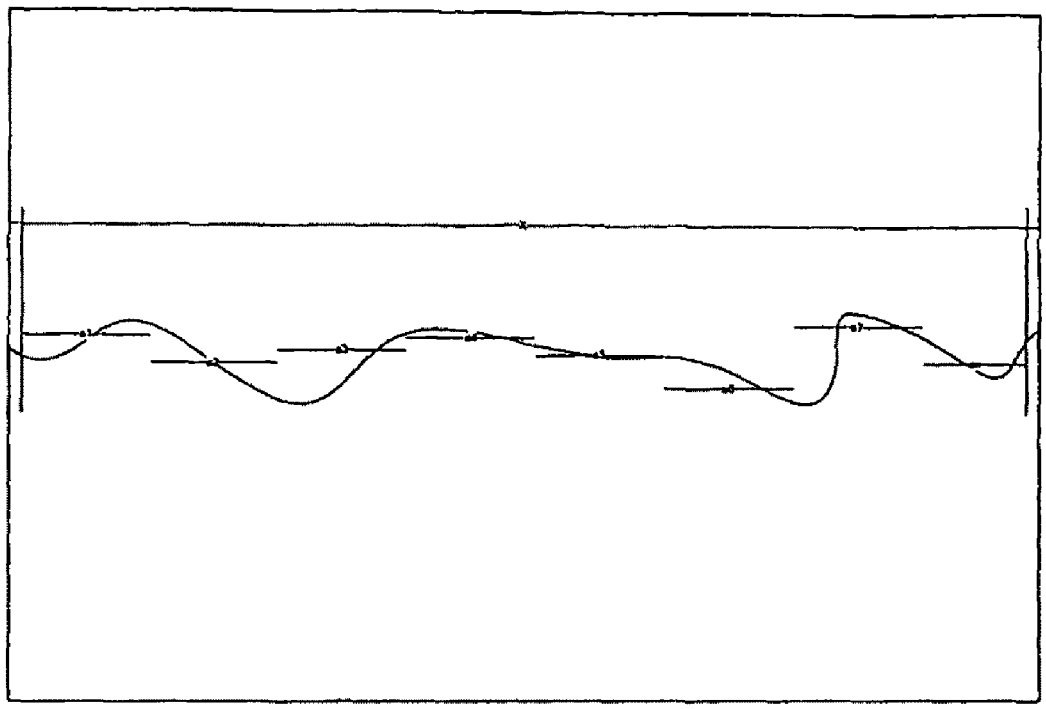
FIGS. 14, 15, 16 and 17 are signal sequence diagrams to illustrate the setting procedure and the monitoring procedure.

With reference to FIG. 14, a process for setting the limit value is described. In order to set a limit value for the alarm, a method is used that involves intermediate storage over a time period x of a number n of average values am, where m=1 to n, each of which are produced from an averaging of continuous measurements made in a respective part (m) of the time period x. At the end of the time period x, the intermediately stored average values are examined, and the highest average value that is found during the time period x is stored as a limit value for subsequent use. The time period for x will typically be in the range of 10 seconds-1 minute. The sub-time period for continuous measurement for calculating the average value a will typically be in the range of 1-10 seconds.

In practical use of the invention, the process for setting the limit value is started by an operator depressing a switch connected to the microcontroller, and the process runs throughout the time x. During the time x, the patient must move his hand in a natural manner so that a tightening and slackening of the strain gauge takes place. In this way a limit value for the "normal" signal level is established, and is used in the detection process to filter away "movement noise".

In addition to the limit value, the operator is given the opportunity to set an "offset value" y, which offsets the detection limit value in order optionally to prevent the alarm from being triggered even through the limit value set by the aforementioned process is reached.

Figure 15:
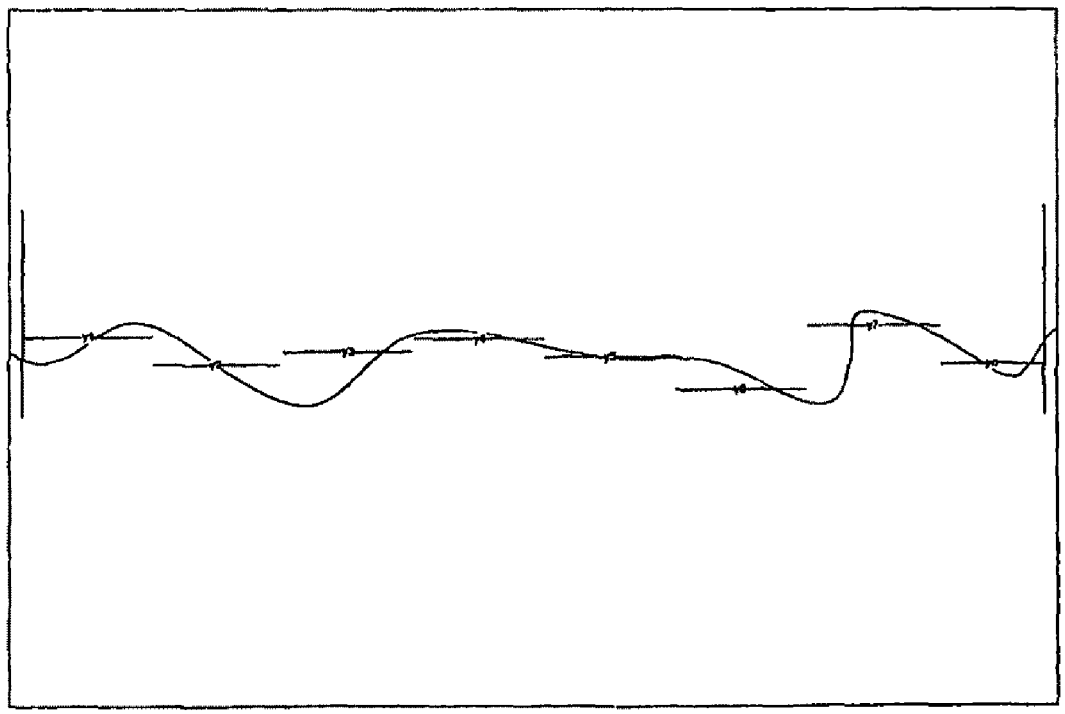

With reference to FIG. 15, a process will now be described for processing signals during the monitoring of the patient. The actual measurement of the tension in the sensor that gives the alarm must be done in a similar way as the calibration of the limit value. An average value over a time period y is computed on the signal, thereby filtering the extreme values away. The average values y which over a considerable period of time have a value that exceeds the limit value, represent an abnormal condition, and will cause an alarm to be triggered and an alarm signal to be transmitted.

Implementation of average measurements for establishing average values a or y as mentioned above are preferably done using the following formula:

$$\text{Average} = \frac{(\text{Average} * k) + \text{New value}}{k+1}$$

The factor k may, for example be 2000. This will result in the latest value being weighted less than the average value.

Figure 16:
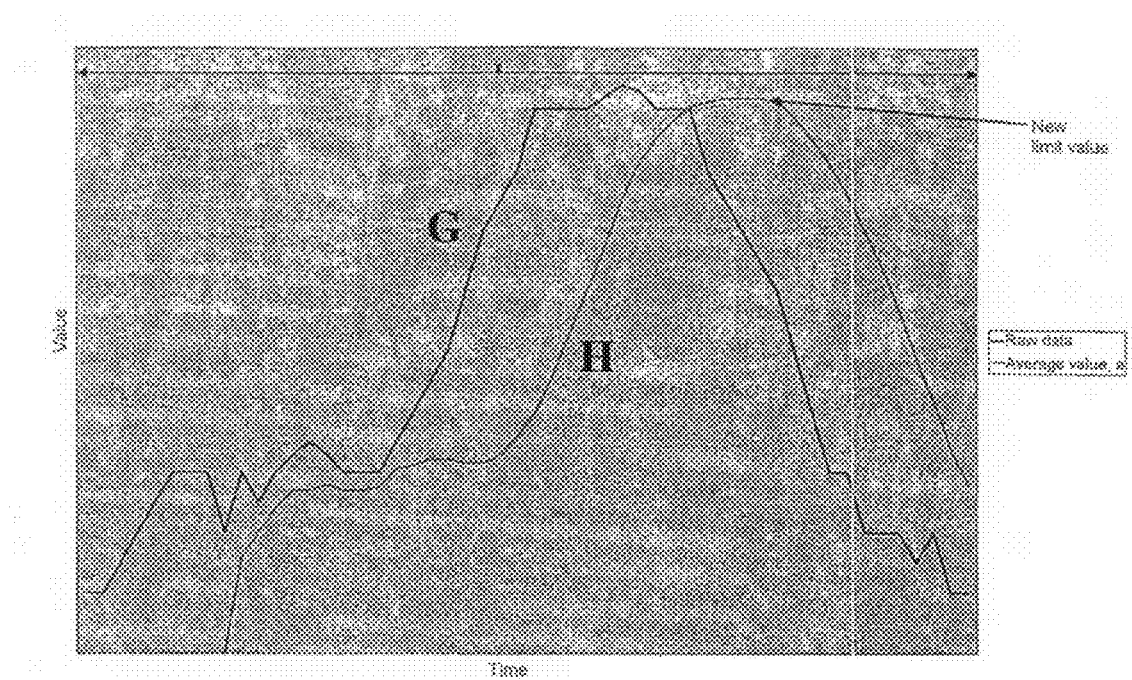

Reference is now made to FIG. 16, for an explanation of an example of an alternative method for setting a limit value—z, for when an alarm is to be triggered. Here, a procedure is used that involves the storing away over a time period x of an average value a, represented by the curve H. The highest value of the average value a, of the raw data represented by the curve G, will in the time period x be stored away as a limit value. The average value is computed as described under point 5. The time constant for x will typically be in the range of 10 seconds-1 minute. The time constant for a will typically be in the range of 1-10 seconds. The procedure is started in that a switch is depressed and it lasts throughout the time x. During the time x, the patient must move his hand in a natural manner so that tightening and slackening occur in the strain gauge. In this way, movement noise will be filtered away.

In addition to the limit value, an offset value b can be set which prevents an alarm from being triggered even though the limit value is reached.

The limit value z will thus be the highest value of a in the time period x added to the offset value b.

A correct adaptation to/of the procedure, the safety bandage, and the placement of the bandage, will enable the abnormal condition to be detected by this procedure by detecting the swelling which gives a larger signal than the natural movement of the hand gives.

Figure 17:
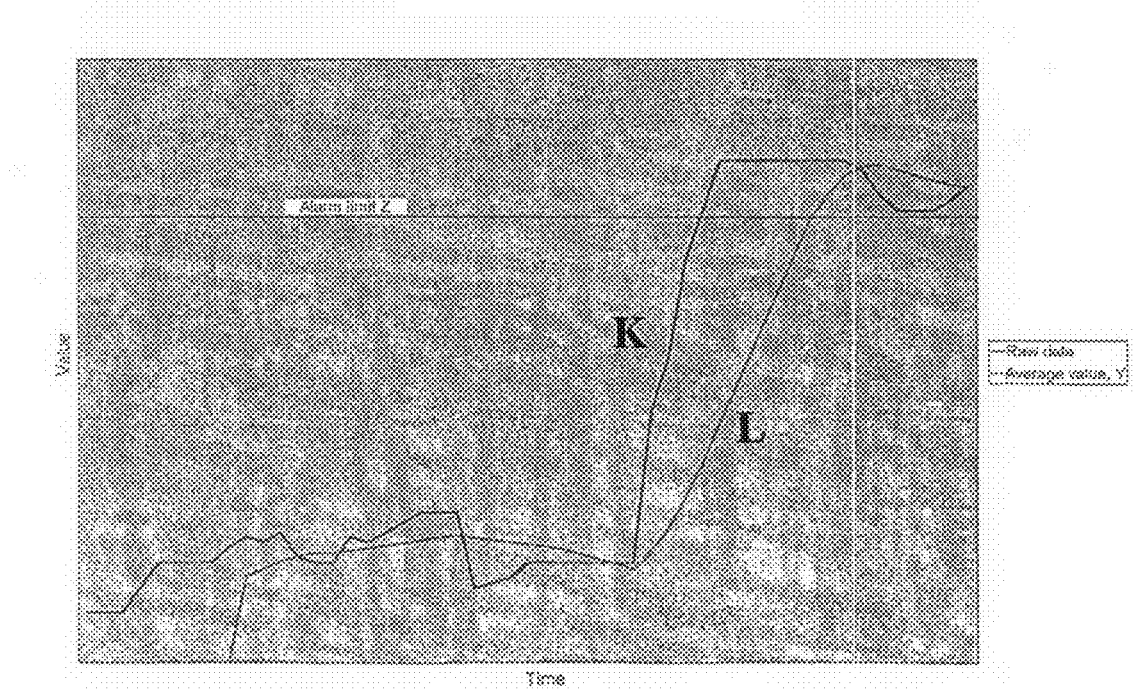
Figure 19A:
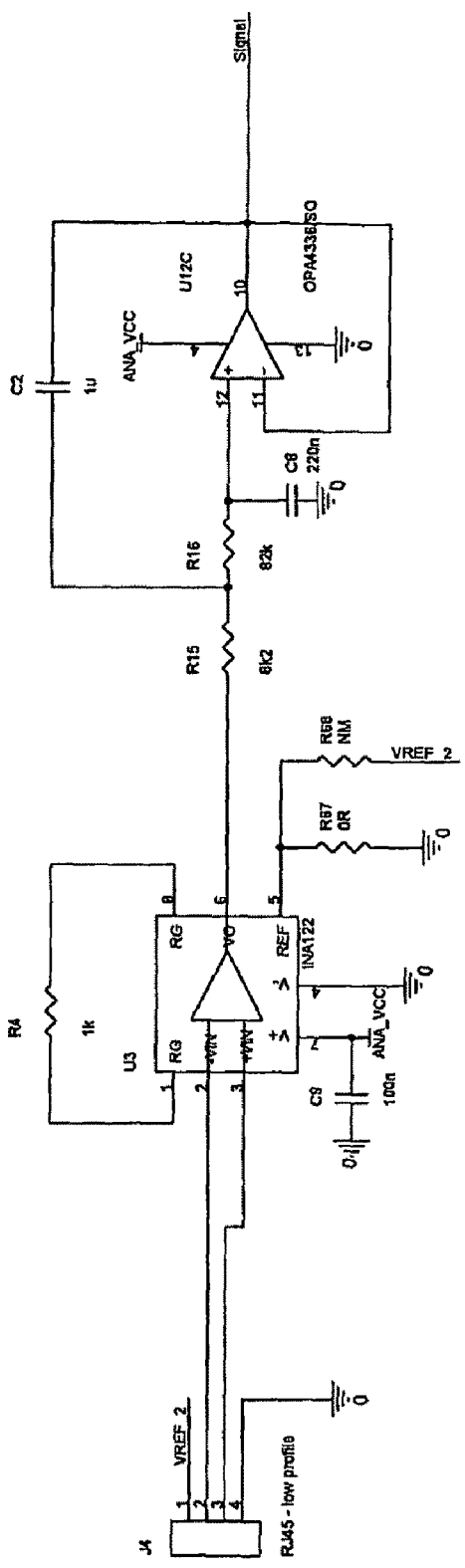
Figure 19B:
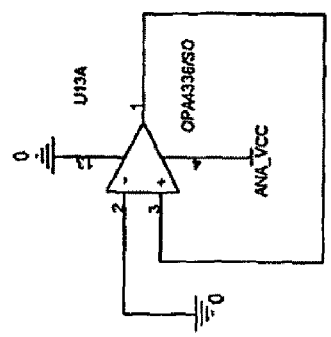
Figure 19C:
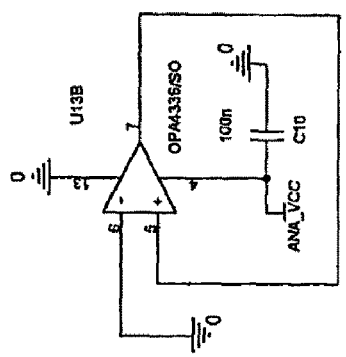
Figure 19D:
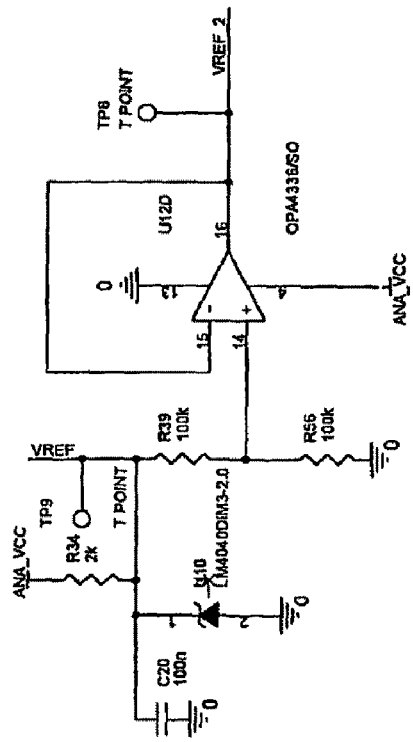

Referring now to FIG. 17, for an explanation of an example of the actual measurement of the tension in the sensor that gives an alarm, this is done in a similar manner as the calibration of the limit value. An average value y, represented by the curve L, over a time period is computed on the signal, raw data represented by the curve K, by using a calculation of averages for averaging, as described by the formula above. In this way, the extreme values are filtered away.

If the mean value y over a considerable time period has a value that exceeds the limit value z, an alarm is triggered and an alarm signal is transmitted.

A set of processes and procedures for the microcontroller is also illustrated in FIG. 21.

In a preferred embodiment of the invention, the safety bandage is made as shown in FIG. 18. FIG. 18a shows a central portion of the bandage in plan view, and FIG. 18b shows a partial section to explain its layered structure. Unlike the safety bandage explained earlier with reference to FIG. 1, and also explained with reference to FIGS. 2 to 5 inclusive, this embodiment (see FIG. 18) is made using an elongate strip or band of a substantially non-extendible but nevertheless flexible material. The material, that is to say the band or strip, which is designated "film" in the drawing in FIG. 18, is of a type that is easy to bend to form a bandage to partly or wholly surround a body part where the PCI has been carried out, but which cannot be stretched in its longitudinal direction to any significant extent. It may be advantageous to use a transparent material, such as a transparent plastic material, which makes it possible to observe the part of the patient that is under the bandage. Preferably, at least parts of the surface of the film that is to be oriented towards the patient should be provided with a friction coating to prevent unintentional displacement of the safety bandage after it has been placed on the patient. This friction coating may, for example, be made by applying an adhesive coating. For practical use, the adhesive coating will be covered by a cover film which can be pulled away immediately prior to application of the safety bandage on the patient. The adhesive coating may advantageously be obtained by applying to the safety bandage film a two-sided adhesive tape with a cover layer that can later be pulled off. The use of an adhesive layer as friction means also results in the safety bandage being held in place on the patient with or without the safety bandage fully surrounding the body part where the PCI was carried out.

The use of a friction means on the surface of the safety bandage film that will come into contact with the patient, and especially the use of an adhesive means, has been found to be favourable for the sensitivity of the invention with respect to its capacity to detect an abnormal condition in the area of the patient where the PCI has been carried out.

By using a film, strip or band of a substantially rigid, but flexible and solid material, such as a plastic material or the like, as an alternative to using the previously mentioned elastic material of a woven type for a safety bandage, it is possible to avoid any bleeding, which could result in the deposit of blood in the elastic fabric, from having an effect on the elasticity of the woven material.

The invention claimed is:

1. A PCI entry site pressure bandage device or safety bandage device provided with fastening means for the device's placement at a PCI entry site and adapted to detect a haematoma or subcutaneous haemorrhage at said PCI entry site, comprising:
   a pressure bandage part; and
   a detection means for detecting a haematoma or subcutaneous haemorrhage at the PCI entry site after a PCI,
   wherein the detection means includes an elongate, bending flexible and, in its longitudinal direction, substantially non-elastic element, to which element there is fastened a strain sensor arranged so that it emits a signal that is indicative of the haematoma or haemorrhage when the element, after the placement of the bandage over the entry site, is subjected to an increase in tension as a result of the occurrence of the haematoma or other swelling from subcutaneous haemorrhage after the PCI.

2. The bandage device according to claim 1, wherein the compression bandage part and the elongate, bending-flexible and, in its longitudinal direction, substantially non-elastic element are formed of at least one uniform, bending flexible but, in its longitudinal direction, substantially non-elastic film, strip or band, formed of a solid material.

3. The bandage device according to claim 2, wherein the solid material is a plastic material, preferably transparent in an area that comprises or surrounds an area of the bandage device designated to be placed immediately over or immediately against the entry site.

4. The bandage device according to claim 2, wherein the film, strip or band has on opposite sides respective first and second surfaces,
   the strain sensor is attached to the first surface, and
   a friction means or an adhesive means with an exposable friction or adhesive surface is attached to the second surface.

5. The bandage device according to claim 4, wherein the exposable friction or adhesive surface is covered by a removable protection.

6. The bandage device according to claim 4, wherein the fastening means is constituted by an adhesive agent.

7. The bandage device according to claim 1, wherein the pressure bandage part consists of an elastic bandage, and
   the elongate, bending flexible and, in its longitudinal direction, non-elastic element is formed of a bendable and, in its longitudinal direction, substantially non-elastic wire woven into the elastic bandage.

8. The bandage device according to claim 7, wherein the wire is a metal wire or spring metal wire.

9. The bandage device according to claim 1, wherein the strain gauge is electronic.

10. The bandage device according to claim 1, further comprising a transmitter device for connection to the strain sensor, and a processing means provided to process an electronic strain gauge signal.

11. The bandage device according to claim 10, wherein the processing means is provided to compute a plurality of first average values of the strain gauge signal over a first time period and to select a largest of the first average values as a threshold value for detection of haematoma or haemorrhage on the basis of measurement of a subsequent strain gauge signal.

12. The bandage device according to claim 11, wherein the processing means is provided to compute a plurality of second average values of the subsequent strain sensor signal over a second period of time and to select one of the second average values which exceed the threshold value as indication of haematoma or haemorrhage.

13. The bandage device according to claim 10, further comprising a receiver device for connection to the transmitter device and comprising an alarm device for emitting an acoustic or optical alarm signal on the basis of a processed strain sensor signal emitted from the processing means.

14. The bandage device according to claim 13, wherein the acoustic signal is a high-frequency acoustic signal.

15. The bandage device according to claim 1, wherein the detection device comprises or is constituted of an optical sensor, with or without optical transillumination and/or illumination of the skin, in order to be able to detect with optical means the haemorrhage in the surrounding tissue, or to be able to discover the haemorrhage possibly even before a swelling occurs to such an extent that it can be detected by a strain sensor.

16. The bandage device according to claim 1, wherein the detection device comprises or is constituted of a temperature sensor for registering a change in temperature in connection with an extravasation of blood into the skin, or to be able to discover the haemorrhage possibly even before a swelling occurs to such an extent that it can be detected by a strain sensor.

17. The bandage device according to claim 1, wherein the PCI pressure bandage is elongate, and
   the fastening means comprises a hook and loop device or an elastic device, arranged at least one end portion of the elongate PCI pressure bandage.

18. The bandage device according to claim 1, wherein the PCI entry site is at the radial artery, about 5-7 cm from the wrist, or at the femoral artery, the main artery in the groin.

19. A production method, comprising:
   assembling a PCI entry site pressure bandage or safety bandage according to claim 1 for use in detecting and warning of a haematoma or subcutaneous haemorrhage after a PCI.

20. A production method for producing a PCI entry site pressure bandage device or safety bandage device adapted to detect a haematoma or subcutaneous haemorrhage at said PCI entry site, comprising:
   combining a PCI entry site pressure bandage part or safety bandage part and an electronic detection device to produce a device designed to both be able to be placed as a PCI entry site pressure bandage or safety bandage over a PCI entry site and to detect an increase in tension as a result of the occurrence of a haematoma or subcutaneous haemorrhage when the bandage is placed over the PCI entry site,
   wherein the detection device comprises a strain sensor attached to an elongate, flexible and, in its longitudinal direction, substantially non-elastic element.

21. The production method according to claim 20 wherein the detection device comprises an optical sensor, with or without optical transillumination and/or illumination of the skin, to be able to register with optical means the haemorrhage in the surrounding tissue, or comprises a temperature sensor for registering a change in temperature in connection with an extravasation of blood in the skin.

22. The production method according to claim 19, wherein the pressure bandage or safety bandage part is formed of an elastic bandage or at least one uniform, bending flexible, but in its longitudinal direction substantially non-elastic film, strip or band, formed of a solid material.

* * * * *